United States Patent [19]

Tomioka et al.

[11] Patent Number: 4,983,359

[45] Date of Patent: Jan. 8, 1991

[54] APPARATUS FOR MEASURING LYMPHOCYTE SUBCLASSES

[75] Inventors: Atsuo Tomioka, Chatsworth, Calif.; Hiroyuki Harada; Keiichi Inami, both of Hyogo, Japan

[73] Assignee: TOA Medical Electronics Co., Ltd., Kobe, Japan

[21] Appl. No.: 95,894

[22] Filed: Sep. 14, 1987

[30] Foreign Application Priority Data

Feb. 10, 1987 [JP] Japan .................... 62-28945

[51] Int. Cl.$^5$ .............. G01N 21/00; G01N 33/00; G01N 33/533

[52] U.S. Cl. .................... 422/81; 356/39; 356/73; 435/808; 436/56; 436/546; 436/805; 436/808

[58] Field of Search ............ 436/56, 501, 546, 805, 436/808; 422/44, 81; 435/2, 4, 7, 808; 356/73, 39

[56] References Cited

U.S. PATENT DOCUMENTS

| | | | |
|---|---|---|---|
| 4,128,628 | 12/1978 | Brooker et al. | 436/805 |
| 4,271,123 | 6/1981 | Curry et al. | 436/805 |
| 4,284,412 | 8/1981 | Hansen et al. | 436/805 |
| 4,500,641 | 2/1985 | Van Den Engh et al. | 356/73 |
| 4,596,035 | 6/1986 | Gershman et al. | 382/6 |
| 4,662,742 | 5/1987 | Chupp | 356/73 |
| 4,667,830 | 5/1987 | Nozaki, Jr. et al. | 356/39 |
| 4,668,617 | 5/1987 | Furuta et al. | 435/4 |
| 4,717,655 | 1/1988 | Fulwyler | 435/7 |
| 4,727,020 | 2/1988 | Recktenwald | 436/72 |
| 4,778,593 | 10/1988 | Yamashita et al. | 356/39 |
| 4,778,763 | 10/1988 | Makiguchi et al. | 436/172 |

FOREIGN PATENT DOCUMENTS

| | | | |
|---|---|---|---|
| 3531891 | 3/1986 | Fed. Rep. of Germany | 436/805 |
| 0094245 | 7/1981 | Japan | 436/805 |

Primary Examiner—Robert J. Warden
Assistant Examiner—Kimberly A. Trautman
Attorney, Agent, or Firm—Pearne, Gordon, McCoy & Granger

[57] ABSTRACT

A blood sample is prepared by combining a fluorescently tagged monoclonal antibody with blood cells. The sample is then passed through a flow cytometer and light scattered by each blood cell in two directions is sensed simultaneously by a single sensor. Lymphocytes are discriminated from other cells by using an intensity distribution of the total scattered light. Then, by using a distribution of fluorescent light intensity of each cell thus discriminated, the cells in a lymphocyte subclass of interest are enumerated with a high accuracy. The data acquired are utilized in diagnosing immunological incompetence or the like.

2 Claims, 6 Drawing Sheets

RELATIVE INTENSITY OF SCATTERED LIGHT

RELATIVE INTENSITY OF FLUORESCENT LIGHT

APPARATUS FOR MEASURING LYMPHOCYTE SUBCLASSES

BACKGROUND OF THE INVENTION

1. Field of the Invention:

This invention relates to the measurement and quantification of lymphocyte subclasses or subpopulations. More particularly, the invention relates to a method and an apparatus for measuring, based on the principle of flow cytometry, blood cells to which fluorescently tagged monoclonal antibodies are bound for identifying lymphocyte subclasses.

2. Description of the Prior Art:

The white blood cells in the blood of a healthy individual include a variety of lymphocytes, monocytes and granulocytes (neutrophils, eosinophils and basophils). Among these, lymphocytes are composed of a plurality of subclasses such as B cells, T cells, N cells and K cells. The T cells can be further divided into such subtypes as helpers, suppressors and killer T cells. Measuring the relative numbers of these lymphocyte subclasses and constituent cells is useful in diagnosing immunological incompetence and in ascertaining the condition of various immunoregulatory disorders. It is also useful in observing the progress of medical treatment of various illnesses.

Each subclass of lymphocyte is characterized by an antigenic determinant on the surface of the cells belonging to the subclass. These antigenic determinants can be identified by specific monoclonal antibodies uniquely bound to the respective antigenic determinants. Examples of monoclonal antibodies for identifying T cells include CD2 (OKT11, Leu-5), CD3 (OKT3, Leu-4) and CD5 (OKT1, Leu-1). An example of a monoclonal antibody for identifying B cells is CD20 (B1). Further, an example of a monoclonal antibody for identifying T cells is CD4 (OKT4, Leu-3).

If these monoclonal antibodies are fluorescently tagged and reacted with blood cells and the fluorescence due to the fluorescent stain is examined, the lymphocytes that belong to a specific subclass can be detected.

A method of identifying and quantifying lymphocyte subclasses based on the principle of flow cytometry using fluorescently tagged antibodies is disclosed in e.g. the specification of Japanese Patent Application Laid-Open Publication (KOKAI) No. 56-16872. In order to identify lymphocytes in accordance with the disclosed method, signal processing is performed in which a two-dimensional signal strength distribution is displayed using signals on two channels, and a two-dimensional specific region in which lymphocytes are present is determined and enclosed.

A problem with the conventional method described above is that the signal processing for automatically determining and enclosing a specific region in the two-dimensional signal strength distribution in which the lymphocytes are present is extremely complicated and is not suited to an apparatus for identifying and quantifying lymphocyte subclasses automatically.

Though the construction of the apparatus and the procedure are greatly simplified if only one type of signal, e.g. side-scattered light only, is used to distinguish lymphocytes based on the signal strength distribution, isolating the lymphocytes from the ghosts of white or red blood cells is unsatisfactory.

The specification of Japanese Patent Application Laid-Open Publication (KOKAI) No. 60-36960 discloses a method of distinguishing lymphocytes among white and red blood cells by combining measured values of forward-scattered light and side-scattered light detected when blood cells are irradiated with light, and converting these measured values into a one-dimensional parameter. However, effecting the conversion into a one-dimensional parameter is a complicated task requiring a voluminous amount of hardware and software. It is also necessary to make the conversion one blood cell at a time, thus requiring an exorbitant amount of time to measure a single blood sample. As a result, the method is not practical for application to an automated apparatus.

SUMMARY OF THE INVENTION

The present invention is directed to solving the aforementioned difficulties encountered in the prior art and is adapted so as to make possible the identification of lymphocytes by processing only one type of signal using only one sensor to sense light scattered in two directions, as a result of which the measurement of lymphocyte subclasses can be automated with ease.

Thus, an object of the invention is to provide a method and apparatus for identifying and quantifying lymphocyte subclasses fully automatically after a sample has been supplied to the apparatus.

According to the present invention, the foregoing object is attained by providing a method of measuring lymphocyte subclasses comprising the steps of: mixing and reacting a fluorescently tagged monoclonal antibody with a blood sample; feeding the sample obtained to a sensing station of a flow cytometer; irradiating the sample with laser light in the sensing station; sensing, by a single photosensor, first scattered light scattered by each cell of the sample in a direction substantially perpendicular to the sample flow direction and parallel to the optical axis of the laser light, and second scattered light scattered by each cell of the sample in a direction perpendicular to the optical axis of the laser light and the sample flow direction; sensing fluorescent light emitted by each cell of the sample in a direction perpendicular to the optical axis of the laser light and the sample flow direction; discriminating lymphocytes based on a distribution of signals indicative of the intensities of the sensed first scattered light and second scattered light; identifying a lymphocyte subclass based on a distribution of signals indicative of the intensity of the sensed fluorescent light corresponding to the lymphocyte; and calculating the positivity of the lymphocyte subclass using the distributions of the signals indicative of the intensities of the scattered light and fluorescent light.

An apparatus for practicing the above-described measurement method comprises: automatic staining means for mixing and reacting a fluorescently tagged monoclonal antibody with a blood sample; a sensing station of a flow cytometer for receiving the sample obtained; a laser light source of irradiating the sensing station with laser light; a single scattered light sensor for sensing first scattered light in a direction substantially parallel to the optical axis of the laser light, and second scattered light in a direction perpendicular to the optical axis of the laser light; a single fluorescent light sensor for sensing fluorescent light in a direction perpendicular to the optical axis of the laser light; data processing means for receiving and processing output signals from the scattered light sensor and fluorescent light sensor; and display means for displaying data indicative of a lymphocyte subclass identified by the data processing means. The automatic staining means comprises an incubator having a plurality of mixing and reacting stations, and an antibody container for individually accommodating plural types of monoclonal antibodies.

The invention as set forth above has a number of advantages:

(1) Lymphocytes can be distinguished by sensing light scattered in two directions using only a single sensor and processing signals of a single type. This makes it possible to simplify the construction of the measurement apparatus and significantly raise the processing speed. This in turn facilitates the full automation of the apparatus.

(2) It is possible to incubate a plurality of samples simultaneously and in parallel fashion at regular intervals. This affords a further increase in processing speed.

(3) A plurality of monoclonal antibodies can be added to, mixed and reacted with a single sample with facility, so that the positivity of a plurality of lymphocyte subclasses of interest can be measured at one time in simple fashion.

Other features and advantages of the present invention will be apparent from the following description taken in conjunction with the accompanying drawings.

BRIEF DESCRIPTION OF THE DRAWINGS:

FIGS. 3 through 6 illustrate examples of measurements using whole blood as a sample, in which FIGS. 3 and 5 are histograms of scattered light intensity signals and FIGS. 4 and 6 are histograms of fluorescent light intensity signals; FIGS. 9 and 10 show the results of measurement using a sample solely of lymphocytes prepared by separation, in which FIGS. 7 and 9 are histograms of scattered light intensity signals and FIGS. 8 and 10 are histograms of fluorescent light intensity signals.

DESCRIPTION OF THE PREFERRED EMBODIMENT

A preferred embodiment of the invention will now be described in detail, though the invention is in no way limited to the illustrated embodiment.

The sample used in the illustrated embodiment may be whole blood containing an anticoagulant, a sample of mononuclear cells prepared by separation, or a sample solely of lymphocytes prepared by separation. One example of a method of separating mononuclear cells is the Ficoll-Hypaque method, which entails adding PBS (phosphate buffer solution) to the buffy coat, stratifying and centrifuging the Ficoll-Hypaque solution, and extracting a layer of an intermediate white band-shaped ring. Lymphocytes and monocytes can thus be separately acquired. In order to obtain a sample of lymphocytes only, the sample of isolated mononuclear cells is passed through a fiber column so that the monocytes will be adsorbed by the fibers.

Figure 1:
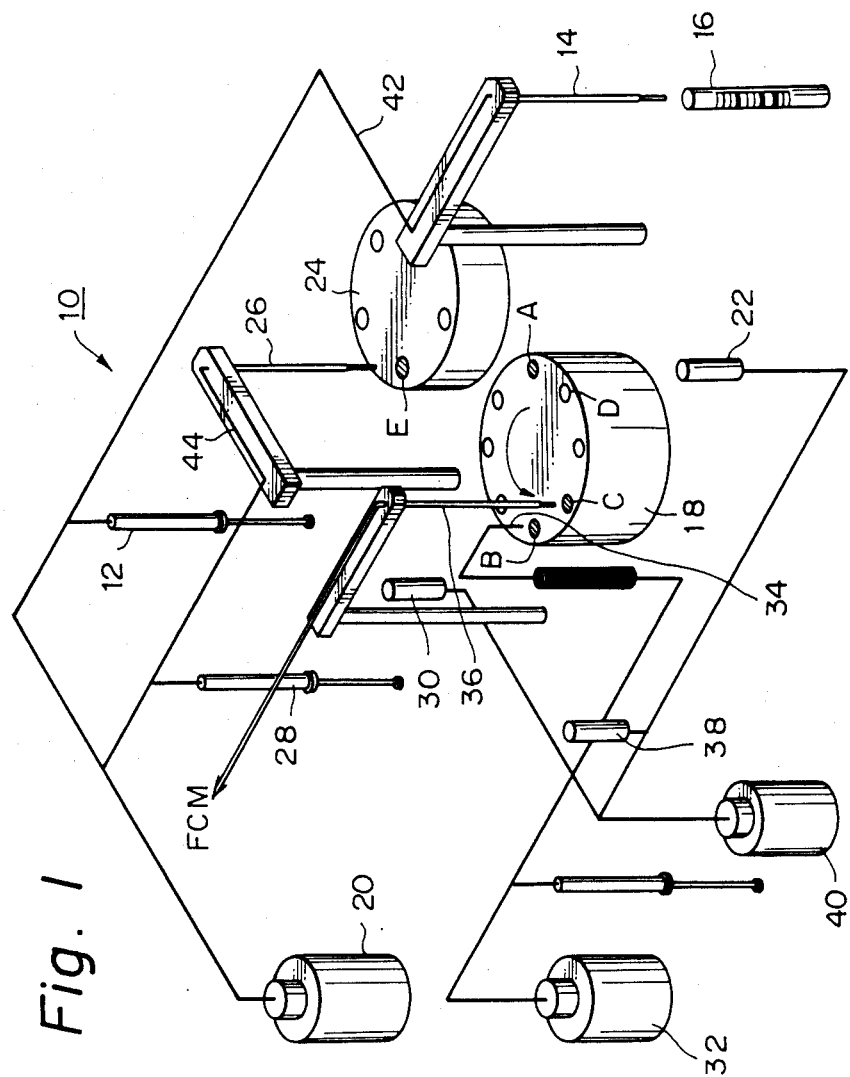
FIG. 1 is a schematic view showing the basic construction of an embodiment of a measurement method and apparatus used in the present invention.

The staining of the sample and the lysing treatment thereof are performed by an automatic staining apparatus 10 shown in FIG. 1.

The automatic staining apparatus 10 includes a syringe 12 which is lowered to a predetermined position so that a blood sample will be taken up from a sample vessel 16 by a pipette 14. The latter is then swung to the position of an incubator section A of an incubator 18, after which the syringe 12 is raised to a predetermined position in order to discharge the prescribed amount of the sample into section A. At the same time, PBS supplied by a phosphate buffer solution tank 20 and filling a conduit 42 is also discharged into the section A, whereby the PBS and blood sample are stirred.

When the sample discharge is completed, the pipette 14 is swung over to a washing bath 22 in which the both the interior and exterior of the pipette are washed. The pipette 14 is then returned to the position shown in FIG. 1 in preparation for the next uptake of a sample.

The apparatus 10 further includes a monoclonal antibody container 24 containing fluorescently tagged monoclonal antibodies for identifying plural types of specific lymphocytes subclasses. The monoclonal antibody container 24 is rotatively indexed to bring one of the monoclonal antibodies contained therein to a position E. A pipette 26 is lowered to the position E, after which a syringe 28 is lowered to a predetermined position so that a prescribed amount of the monoclonal antibody at position E is taken up by the pipette 26. Next, the pipette 26 is swung over to the position of the incubator section A of incubator 18, and the syringe 28 is then raised to a predetermined position to discharge the prescribed amount of the monoclonal antibody together with the PBS filling a conduit 44. The sample at section A is re-stirred. When the sample discharge is completed( the pipette 26 is swung over to a washing bath 30 in which the both interior and exterior of the pipette are washed. The pipette 26 is then returned to the position shown in FIG. 1.

After the above operation, the sample at section A is incubated until the antigen-antibody reaction between the monoclonal antibody and the specific antigen of the lymphocyte subclass identified by the monoclonal antibody has progressed sufficiently.

At the end of incubation, the incubator 18 is rotated to index the sample at position A to a position B. Next, a lysing agent supplied by a lysing agent tank 32, is discharged into the sample at position B through a discharge conduit 34 and the sample is re-stirred, whereby red blood cells are lysed from the sample.

At elapse of a fixed period of time, the incubator 18 is rotated to index the sample at position B to a position C. This is followed by lowering a pipette 36 to the section C, at which the sample is taken up by the pipette, which then proceeds to deliver the sample to a sensing station (FCM) When take-up of the sample ends, the pipette 36 is raised, washed in a washing bath 38 and returned to the position shown in FIG. 1.

The waste liquids resulting from the washing of the various pipettes are collected in a waste tank 40.

The treatments described above are performed successively in accordance with a set time schedule. When measuring samples that differ from one to another, it is of course permissible to measure the next sample after an entire series of treatments applied to one sample end. In order to raise the efficiency of the apparatus, however, it is advisable to start the take-up of the next sample in the course of treating the preceding sample. For example, it is preferred that the incubator 18 be indexed by one step to move the section D to the position A while the sample at section A is being incubated, after which the next sample is taken up by pipette 14 and discharged into the section D (which will be at the position A at this time). It will thus be possible to incubate a plurality of samples simultaneously in parallel fashion at regular intervals.

The sensing station of the flow cytometer of the apparatus will now be described with reference to FIG. 2.

The sensing station of the flow cytometer includes an argon ion laser 46 which emits a light beam focused by a condenser lens 48 so as to irradiate the sample flowing through a flow cell 50 receiving the sample from the automatic staining apparatus 10. The sample flows through the flow cell 50 in a fine stream in a form enveloped by a fluid sheath of the phosphate buffer solution (PBS). The cells in the specimen pass through a sensing zone in which they are irradiated by the laser beam one cell at a time.

As the cells pass through the sensing zone, they scatter the light irradiating them. Some of this light is scattered over a certain angular range from a direction parallel to the irradiating light and is collected by a collector lens 52. Since direct light from the laser light source is stopped by a beam stopper 54, this light does not impinge upon the collector lens 52. The scattered light collected by the collector lens 52 is applied to a regulator 56 adapted to regulate the amount of light. The light so regulated is introduced to an optical fiber 58, which guide the light to a scattered light sensor 60.

Some of the scattered light produced when the cells pass through the sensing zone of the flow cytometer is perpendicular to the optical axis of the laser light beam and the direction of the sample flow. That part of this scattered light within a certain angular range is collected by a collector lens 62. The scattered light collected by the collector lens 62 passes through a pin hole 64 before being reflected by a dichroic mirror 66. The reflected light passes through a filter 68 and is then regulated in terms of quantity before impinging upon a scattered light sensor 60. The dichroic mirror 66 and filter 68 are for the purpose of selecting scattered light only and causing this scattered light to impinge upon the scattered light sensor 60.

The light scattered in the aforementioned two directions is regulated in terms of quantity by one or both of the regulators 56, 70. In either case, the scattered light is incident upon only a single sensor, namely the scattered light sensor 60.

When a cell passes through the sensing zone of the flow cytometer, some of the fluorescent light emitted by the fluorescent stain on the monoclonal antibody travels in a direction perpendicular to the irradiating light and the direction of the sample flow. This part of the fluorescent light is collected by the collector lens 62 in the same manner as the aforementioned scattered light. The fluorescent light so collected is reflected by a total reflecting mirror 72 and then passes through a filter 74, which extracts fluorescent light of a specific wavelength region only. The fluorescent light in this wavelength region is incident upon a fluorescent light sensor 76.

Figure 2:
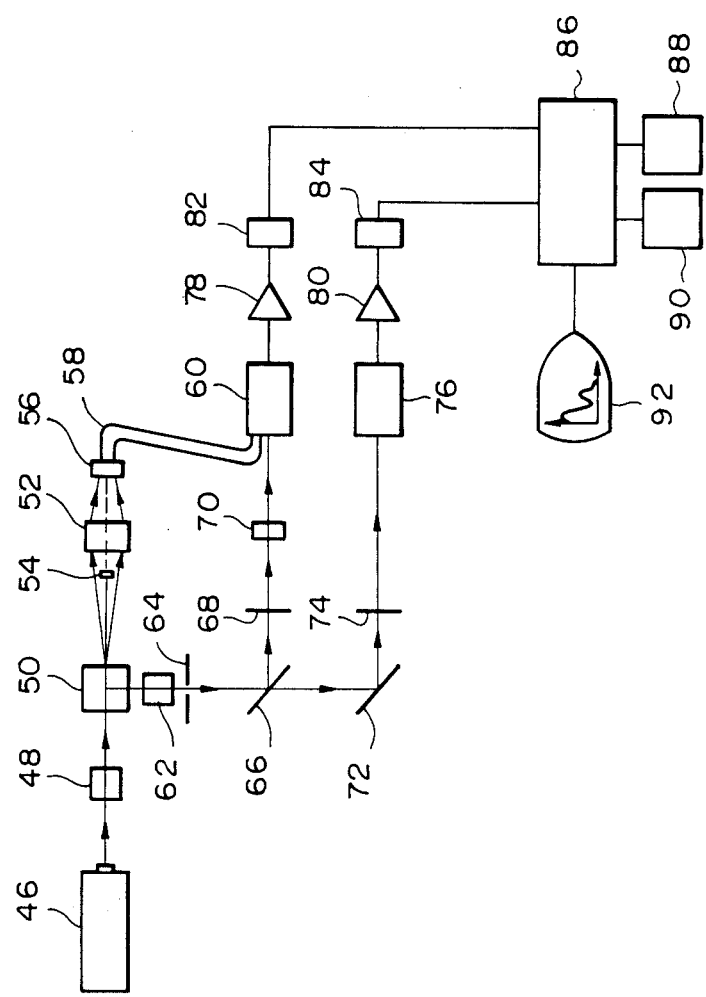
FIG. 2 is a block diagram showing the basic construction of a sensing station in a measurement apparatus according to the present invention.

Note that the arrows shown in FIG. 2 indicate the direction in which light propagates.

The scattered light sensor 60 and the fluorescent light sensor 76 are photoamplifier tubes which convert the light signals incident thereon into electrical signal pulses. These signal pulses are amplified by amplifiers 78, 80 before being delivered to A/D converters 82, 84 that convert the peak values of the signal into digital data applied to a data processor 86.

When the value of scattered light data obtained from the A/D converter 82 is greater than a preset noise level, the data processor 86 renders a decision to the effect that a cell has passed through the sensing zone, stores the data from the A/D converter 82 in a scattered light intensity memory 88, and stores the data from the A/D converter 84 in a fluorescent light memory 90. The scattered light data and fluorescent light data planted in the memories 88, 90 simultaneously are stored in such a manner that they can be dealt with later.

The data processor 86 performs the above-described data storage processing in a fixed period of time with regard to one sample at a time delivered by the automatic staining apparatus 10. As a result, data relating to from several hundred to several tens of thousands of cells ordinarily are stored for each sample.

Figure 3:
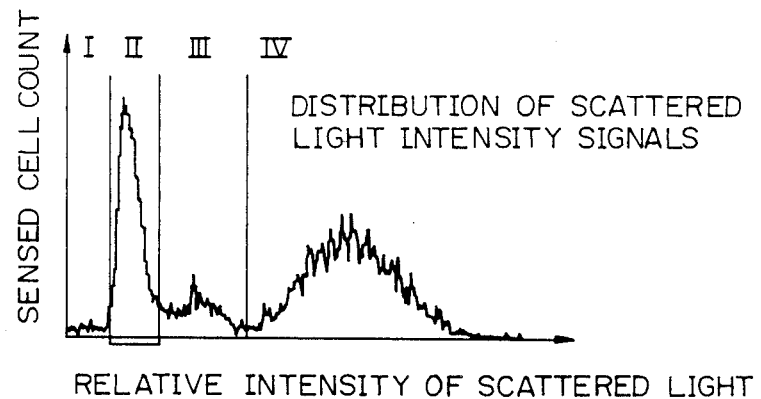

When the processing for storing the data relating to one sample ends, the data processor 86 computes a histogram of scattered light intensity distribution of the kind shown in FIG. 3, regarding the data stored in the scattered light intensity memory 88. In FIG. 3, region I indicates lysed red blood cell ghosts, region II indicates lymphocytes, region III indicates monocytes, and region IV indicates granulocytes. This was verified by comparing the count of the cells belonging to each region with the results of counting the numbers of each of the cells by means of an electric resistance-type blood cell counter. This was further substantiated by the fact that a histogram was obtained solely in region II when a sample having only lymphocytes was measured, and solely in regions II and III when a sample having only lymphocytes and monocytes was measured.

Figure 4:
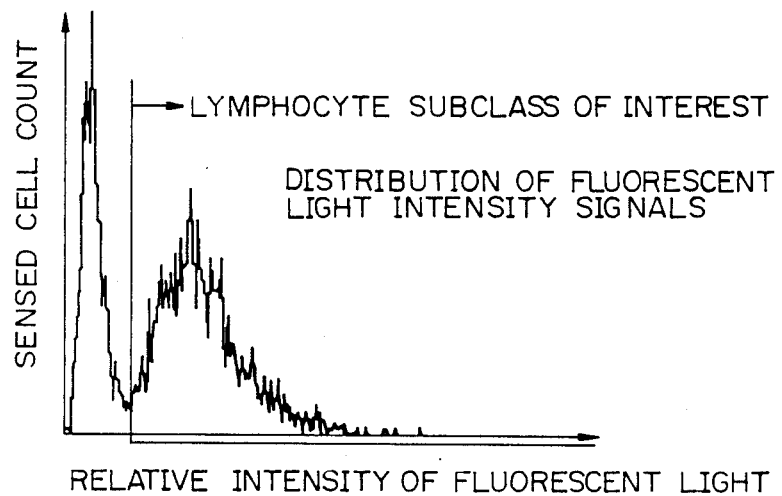

The data processor 86 automatically sets a lymphocyte region (region II) based on the histogram of scattered light intensity shown in FIG. 3, reads the corresponding fluorescent light data, which was stored at the same time as the scattered light data belonging to this region, out of the fluorescent light intensity memory 90, computes an intensity distribution of the kind shown in FIG. 4, and causes this distribution to be displayed on a display unit 92. The data processor 86 is also adapted to sense the valley in the intensity distribution of the histogram shown in FIG. 4, compute the sensed cell count contained in the histogram on the side of the valley having the stronger fluorescent light intensity, obtain the ratio with respect to the total lymphocyte count, and cause the ratio to be displayed on the display unit 92 as the positivity.

An example of a measurement performed by the apparatus of the illustrated embodiment will now be described.

Figure 5:
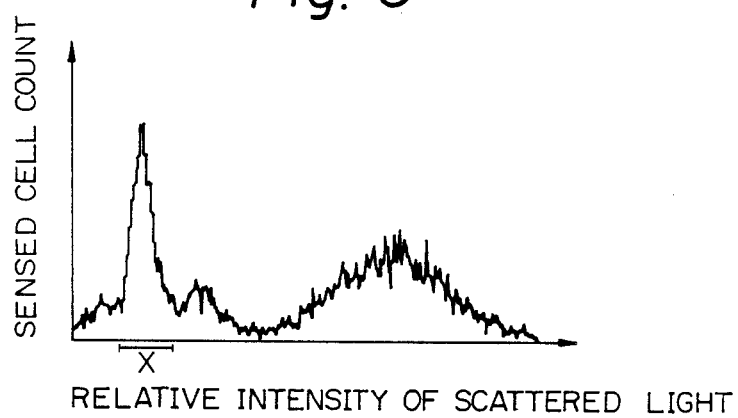
Figure 6:
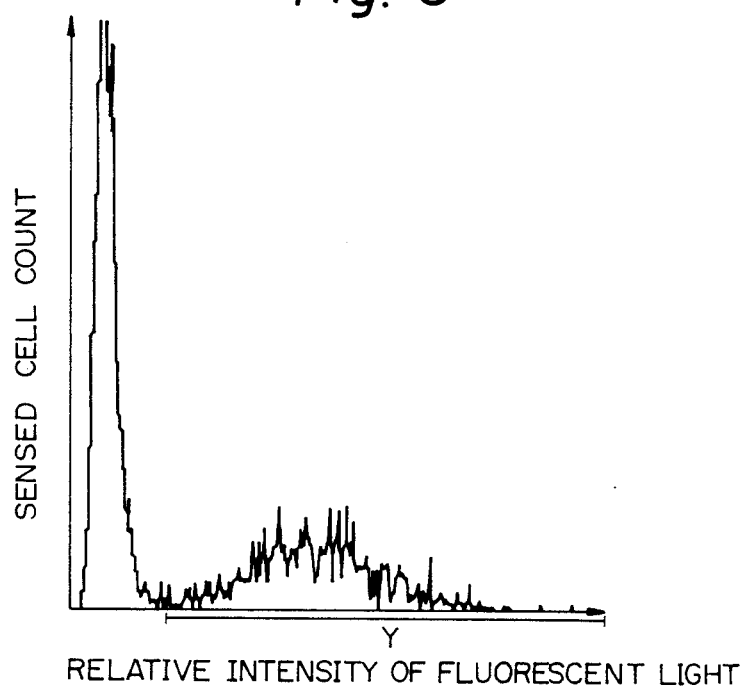

The aforementioned FIGS. 3 and 4 are examples of measurement using whole blood as the sample, in which FIG. 3 illustrates a histogram of scattered light and FIG. 4 a histogram of fluorescent light. In this case the positivity of the lymphocyte subclass which was the object of measurement was 64.5%. FIGS. 5 and 6 are also examples of measurement using whole blood as a different sample, in which FIG. 5 illustrates a histogram of scattered light and FIG. 6 a histogram of fluorescent light. FIG. 6 depicts the fluorescent light intensity distribution for cells (lymphocytes) contained in the underlined portion X of FIG. 5. The positivity of the lymphocyte subclass of interest contained in the underlined portion Y of FIG. 6 was 40.2%.

Figure 7:
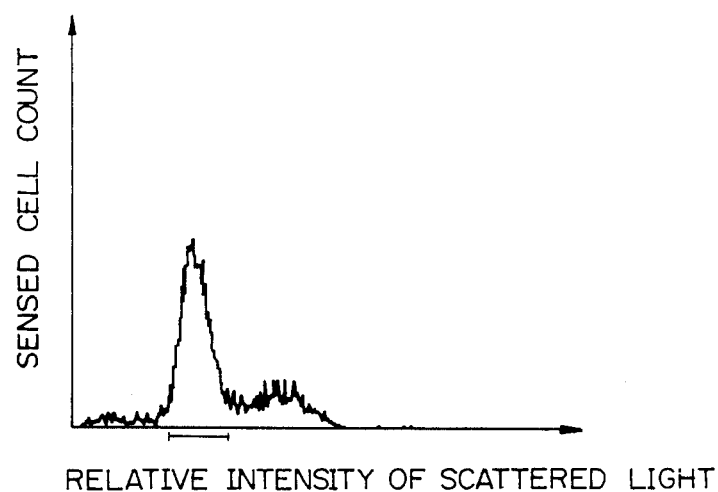
FIGS. 7 and 8 show the results of measurement using a sample of mononuclear cells prepared by separation.
Figure 8:
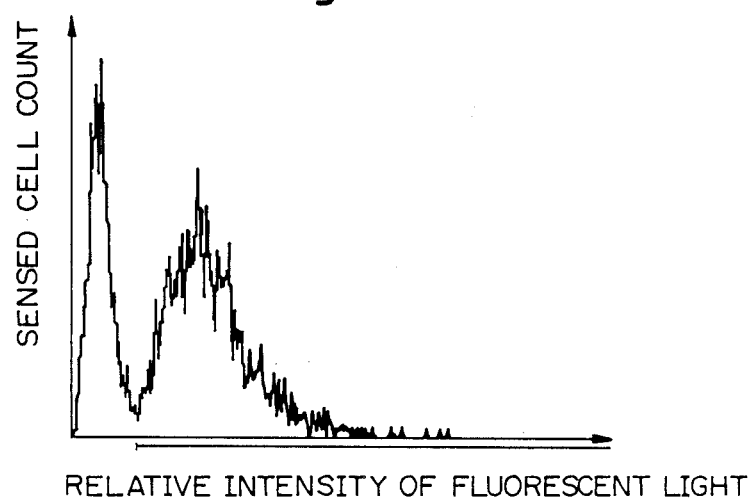
Figure 9:
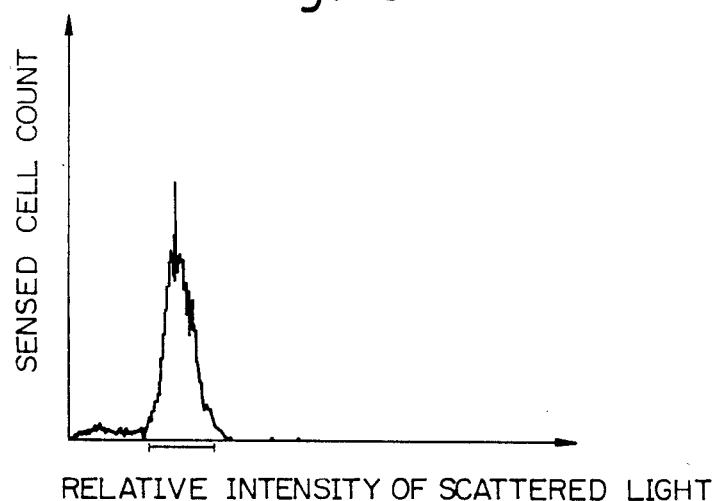
Figure 10:
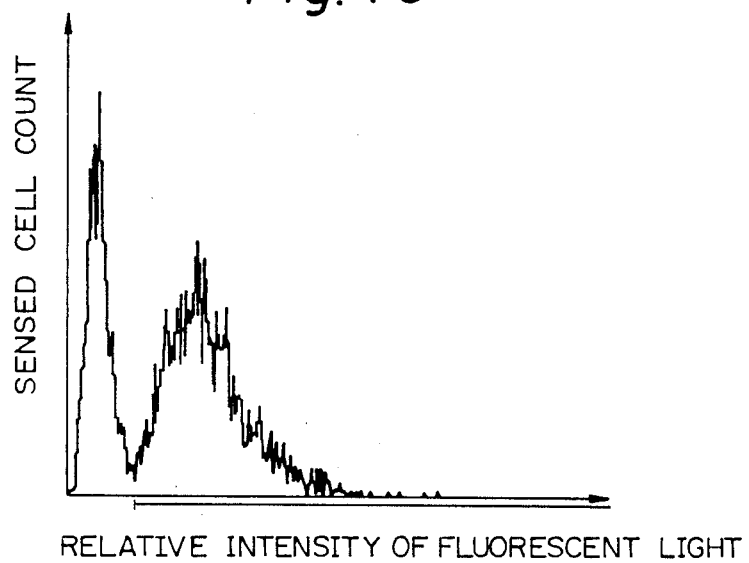

FIGS. 7 and 8 show the results of measurement using a sample of mononuclear cells prepared by separation, and FIGS. 9 and 10 show the results of measurement using a sample solely of lymphocytes prepared by separation. FIGS. 7 and 9 are histograms of scattered light, and FIGS. 8 and 10 are histograms of fluorescent light from lymphocytes.

The illustrated embodiment deals with a case where one type of monoclonal antibody is added to one sample. However, the addition of a plurality of monoclonal antibodies to one sample can be readily achieved by a slight modification of the processing procedure executed by the automatic staining apparatus 10. In such a case, adopting a plurality of channels for handling the fluorescent light intensity signals and partially modifying the processing procedure of the data processor 86 would make it possible to deal with a plurality of the fluorescent light intensity signals and to measure the positivities of plural lymphocyte subclasses of interest.

As many apparently widely different embodiments of the present invention can be made without departing from the spirit and scope thereof, it is to be understood that the invention is not limited to the specific embodiments thereof except as defined in the appended claims.

What is claimed is:

1. An apparatus for measuring lymphocyte subclasses comprising:
   (a) automatic staining means for mixing and reacting a fluorescently tagged monoclonal antibody with a blood sample;
   (b) a sensing station of a flow cytometer including a flow cell through which the stained sample is passed;
   a laser light source for irradiating with laser light the stained sample as it is passed through the flow cell of said sensing station;
   a single photosensor for sensing first scattered light scattered by each cell of the sample in a direction substantially parallel to the optical axis of the laser light, and second scattered light scattered by each cell of the sample in a direction perpendicular to the optical axis of the laser light, said photosensor being located downstream of the irradiation of the cells passing through the flow cell;
   a single fluorescent light sensor for sensing fluorescent light in a direction perpendicular to the optical axis of the laser light, said fluorescent light sensor being located downstream of the irradiation of the cells passing through the flow cell;
   (c) data processing means for receiving and processing output signals from said scattered light photosensor and fluorescent light sensor to discriminate lymphocytes based on a distribution of signals indicative of the intensities of the first scattered light and the second scattered light; and
   (d) display means for displaying data indicative of a lymphocyte subclass identified by said data processing means.

2. The apparatus according to claim 1, wherein said automatic staining means comprises an incubator having a plurality of mixing and reacting stations, and antibody containers for individually accommodating plural types of monoclonal antibodies.

* * * * *